United States Patent [19]
Hain et al.

[11] Patent Number: 5,834,268
[45] Date of Patent: Nov. 10, 1998

[54] STILBENE SYNTHASE GENES FOR GRAPEVINE

[75] Inventors: Rüdiger Hain, Langenfeld; Hans-Jörg Reif, Cologne; Klaus Stenzel, Duesseldorf, all of Germany

[73] Assignee: Bayer Aktiengesellschaft, Leverkusen, Germany

[21] Appl. No.: 602,931

[22] Filed: Feb. 16, 1996

Related U.S. Application Data

[62] Division of Ser. No. 127,097, Sep. 24, 1993, Pat. No. 5,500,367, which is a continuation of Ser. No. 718,507, Jun. 20, 1991, abandoned.

[30] Foreign Application Priority Data

Jun. 29, 1990 [DE] Germany ............................ 40 20 648.3
Mar. 8, 1991 [DE] Germany .............................. 4107396.7

[51] Int. Cl.$^6$ ............................ C12N 15/10; C12N 15/29; C12P 19/34; C12Q 1/68
[52] U.S. Cl. .................. 435/172.3; 435/91.1; 435/172.1; 435/6
[58] Field of Search ................................ 435/91.1, 172.3, 435/172.1, 6

[56] References Cited

U.S. PATENT DOCUMENTS 4,886,937 12/1989 Sederoff et al. ......................... 800/205

FOREIGN PATENT DOCUMENTS 309862 9/1988 European Pat. Off. .

OTHER PUBLICATIONS

FEBS Letters, vol. 268, No. 1, Jul. 30, 1990, pp. 17–20, "Grapevine stilbene synthase cDNA only slightly differing from chalcone synthase cDNA is expressed in *Escherichia coli* into a catalytically active enzyme".

European Journal of Biochemistry, vol. 172, No. 1, Feb. (II), 1988.

Chemical Abstracts, vol. 113, 1990, Aug., pp. 466–467.

Vaeck et al. Nature, vol. 328, Jul. 2, 1987, pp. 33–37, "Transgenic plants protected from insect attack".

Schroder et al. (1988) Eur. J. Biochem. 172: 161–169 "Molecular analysis of resveratrol synthase cDNA, genomic clones and relationship with chalcone synthase".

Fritzemeier et al. (1981) "Coordinate Induction by UV Light of Stilbene Synthase, Phenylalanine Ammonia–lyase and Cinnamate 4–Hydroxylase in Leaves of Vitaceae" Planta 151, pp. 48–52.

Glover, Gene Clonings London: Chapman and Hall pp. 1–21, 1984, "Principals of Cloning DNA".

Lee et al., "Generation of cDNA Probes Directed by Amino Acid Sequence: Cloning of Urate Oxidase," Science vol. 239, pp. 1288–1291, Mar. 11, 1988.

Ausubel et al., (Ed.) *Short Protocols in Molecular Biology—A Compendium of Methods from Current Protocols in Molecular Biology*, New York: Wiley & Sons title page, pp. iii–xvi and 191–194.

*Primary Examiner*—Rebecca E. Prouty
*Assistant Examiner*—Kawai Lau
*Attorney, Agent, or Firm*—Sprung Kramer Schaffer & Briscoe

[57] ABSTRACT

The present invention relates to the gene for stilbene synthase, isolated from plants, and its use for the transformation of vectors, host organisms and plants, as well as to the production of plants which have an increased resistance to pests.

4 Claims, 4 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

(i) SEQUENCE CHARACTERISTICS:
  (A) LENGTH: 41 base pairs
  (B) TYPE: nucleic acid
  (C) STRANDEDNESS: single stranded
  (D) TOPOLOGY: linear (xi) SEQUENCE DESCRIPTION: SEQ ID NO:1:

TATGCTGATT ACTATTTCAG AGTCACTAAG AGCGAGCACA                40

T                                                           41

(2) INFORMATION FOR SEQ ID NO: 2:

(i) SEQUENCE CHARACTERISTICS:
    (A) LENGTH: 36 base pairs
    (B) TYPE: nucleic acid
    (C) STRANDEDNESS: single stranded
    (D) TOPOLOGY: linear (xi) SEQUENCE DESCRIPTION: SEQ ID NO:2:

GACTGAGTTG AAGAAGAAGT TCAATCGCAT ATGTAA                    36

(2) INFORMATION FOR SEQ ID NO: 3:

(i) SEQUENCE CHARACTERISTICS:
    (A) LENGTH: 56 base pairs
    (B) TYPE: nucleic acid
    (C) STRANDEDNESS: single stranded
    (D) TOPOLOGY: linear (xi) SEQUENCE DESCRIPTION: SEQ ID NO:3:

TATGGTAACA TGTCTAGTGC ATGTGTCTTG TTTATTTTGG                40

ATGAGATGAG AAAGAA                                          56

STILBENE SYNTHASE GENES FOR GRAPEVINE

This application is a divisional of application Ser. No. 08/127,097, now U.S. Pat. No. 5,550,367 filed Sep. 24, 1993 which is a continuation of Ser. No. 07/718,507, filed Jun. 20, 1991, now abandoned.

The present invention relates to genes for stilbene synthases, isolated from grapevines, and their use for the transformation of vectors, host organisms and plants, as well as to the production of plants which have an increased resistance to pests.

The term stilbenes describes a group of chemical substances which occur in plants and which contain, as the common basic structure, the stilbene skeleton (trans-1,2-diphenylethylene). This basic skeleton can be complemented by adding further groups. Two important stilbenes are 3,5-dihydroxy-stilbene (pinosylvin) and 3,3',5-trihydroxy-stilbene (resveratrol).

Stilbenes have been found in certain trees (angiosperms, gymnosperms), but also in some herbaceous plants (in species of the families of the Myrtaceae, Vitaceae and Leguminosae). Stilbenes are toxic to pests, in particular to fungi, bacteria, viruses and insects, and are suitable for fighting these pests. The capability of synthesizing these substances can be seen as an important defence mechanism of the plants. Unfortunately, only few useful plants are capable of forming stilbenes, or of producing them in such an amount that it makes them sufficiently resistant to pests.

The use of stilbene synthase genes for producing plants with an increased pest resistance has already been disclosed in EP-A-0,309,862. This publication specifically describes a stilbene synthase gene from peanut plants (*Arachis hypogea*).

There have now been isolated new genes for stilbene synthase ("stilbene synthase genes") from grapevine, and these genes can be incorporated into the genome of plants which produce no stilbenes, or only to an insufficient extent, by which method the resistance of these plants to pests can be increased.

Surprisingly, the new stilbene synthase genes from vine result in considerably more favourable pest resistances in plants than the stilbene synthase gene from peanut, which is already known from the prior art.

Stilbene synthase genes are understood as meaning nucleic acids (DNA) which, after they have been transcribed into RNA and translated into protein (in a suitable environment) cause the formation of an enzyme which has the properties of a stilbene synthase (enzymatic synthesis of stilbene in a suitable environment), these nucleic acids being isolated from their natural environment or being integrated in a vector or being contained in a procaryotic or eucaryotic DNA as "foreign" DNA or as "additional" DNA.

Stilbene synthase genes are also understood as meaning those stilbene synthase genes which contain, at their beginning and/or end, other DNA sequences which do not inhibit the function of the genes, or not to a considerable extent, these DNA sequences which are also termed "gene units", are formed for example by cutting out using restriction enzymes (for example by cleavage with EcoRI in the case of gene 1 and by partial cleavage in the case of gene 2), since no cleavage sites for conventional restriction enzymes exist exactly at the beginning and at the end of the gene. At their ends, the stilbene synthase genes, or the gene units, can also carry those DNA sequences which are in each case suited to their manipulation (for example "linkers").

The stilbene synthase genes (or the gene units) can be present in the form in which they are contained in the plant genome ("genomic" form, including non-stilbene-synthase-encoding and/or non-regulatory sequences (such as introns), or in a form which corresponds to cDNA ("copy" DNA) which can be obtained from mRNA with the aid of reverse-transcriptase/polymerase (and no longer contains introns). The stilbene synthase genes can also be in partly or completely synthesized form. By synthetic genes there are also to be understood genes which are created by the novel fusion of portions of natural genes.

In the stilbene synthase genes (or the gene units) according to the invention, DNA sections can be replaced by other DNA sections, or DNAs, which act essentially in the same direction.

In the present connection, "foreign" DNA is understood as meaning such DNA (in particular genes or gene units, or portions thereof) which does not naturally occur in a certain procaryotic or eucaryotic genome but which is only incorporated into this genome as a result of manipulation by man. "Additional" DNA (in particular genes or gene units, or portions thereof) will be such DNA which does in fact occur naturally in the particular procaryotic or eucaryotic genome, but is only incorporated into this genome in additional amounts as a result of manipulation by man. One or more specimens of the "foreign" DNA or "additional" DNA can be incorporated, depending on the demand and the nature of the case in question.

Stilbene synthase, which is formed in plants or plant cells under participation of the stilbene synthase genes (or the gene units) according to the invention, denotes any enzyme which causes the formation of those vegetable defence substances against pests (phytoalexins) which show a stilbene skeleton.

In the present case, resveratrol is particularly preferred as the stilbene, that is to say, resveratrol synthase is particularly preferred as the stilbene synthase.

As already mentioned, the stilbene synthase genes according to the invention are those which can be isolated from vine, preferably from (Vitis vinifera and Vitis riparia), with Vitis vinifera being preferred, in particular from Vitis vinifera cv. Optima.

Particularly preferred as stilbene synthase genes according to the invention are the stilbene synthase genes which are present (as gene units) in plasmids pVSt1, pVSt2 and pVSt12t3 (which will be described in greater detail below), as well as the DNA sequences which act essentially in the same direction.

The stilbene synthase genes occurring in grapevines (a number of at least 5 genes is assumed) display extensive DNA sequence homology. The stilbene synthase genes contained in plasmid pVSt12t3 are located close to each other in the plant genome (genetic coupling). All the stilbene synthase genes encode for resveratrol synthase, the genes differing from each other essentially by the quantities of the resveratrol synthase formed. The stilbene synthase genes, which are not described in detail in the present text, can be determined, isolated and elucidated in the customary manner using the known methods of molecular biology because of the sequence homology, this being particularly advantageously possible with the aid of the gene DNA sequences located on plasmids pVSt12t3, pVSt1 and pVSt2, because of the homologies.

Particularly preferred stilbene synthase genes or gene units according to the invention are those contained in plasmid pVSt12t3, as well as the DNA sequences which act in essentially the same direction.

A gene according to the invention, named "gene 1" in the following text, is located in the form of a gene unit, named "gene unit 1" in the following text, on plasmid pVSt12t3 on an EcoRI fragment about 4.9 kb in size. Gene unit 1 can also be isolated from the plasmid using BamHI. HindIII cuts within the gene. Gene unit 1 also exists on plasmid pVSt1 and can also be isolated from this plasmid, using the restriction enzymes mentioned.

A further gene according to the invention, named "gene 2" in the following text, is located in the form of a gene unit, named "gene unit 2" in the following text, on plasmid pVSt12t3 on a fragment about 3.4 kb in size, which is obtained by partial digestion with EcoRI. Asp718 cuts within the gene.

A further functional stilbene synthase gene according to the invention is obtained by fusing gene unit 2 at the EcoRI site at 3600 bp of plasmid pVSt12t3 with the EcoRI site at 200 bp of plasmid pVSt12t3. The fragment of gene unit 2 is here completed by the partial sequence of a further gene (gene 3), which is contained, in parts, on plasmid pVSt12t3. The two sub-fragments of genes, or gene units, 2 and 3 are also contained on plasmid pVSt2. The resulting fusion gene is an example of a synthetic gene.

Preferred genes and gene units according to the invention are genes and gene units 1 and 2 and the fusion gene and the corresponding gene unit. Genes and gene units 1 and 2 are particularly preferred.

*Escherichia coli* strain *E. coli* Fier 1 pVSt1 contains plasmid pVSt1. *Escherichia coli* strain *E. coli* Fier 2 pVSt2 contains plasmid pVSt2. *Escherichia coli* strain *E. coli* Fier pVSt12t3 contains plasmid pVSt12t3. These strains were deposited at the Deutsche Sammlung von Mikroorganismen (DSM) [German Collection of Microorganisms], Mascheroder Weg 1b, D-3300 Braunschweig, Federal Republic of Germany, in agreement with the regulations of the Budapest Treaty on the International Recognition of the Deposit of Microorganisms for the Purposes of Patent Procedure (date of deposit: *E. coli* Fier 1 pVSt1 and Fier 2 pVSt2: Jun. 18, 1990 and *E. coli* Fier pVSt12t3: Feb. 11, 1991).

Strain *E. coli* Fier 1 pVSt1 was given Deposit Number DSM 6002, strain *E. coli* Fier 2 pVSt2 was given Deposit Number DSM 6003 and strain *E. coli* Fier pVSt12t3 was given Deposit Number DSM 6346.

These strains as well as their mutants are likewise part of the present invention. The quantities required of plasmids pVSt12t3, pVSt1 and pVSt2, which are deposited in these hosts, can readily be obtained in the customary manner by multiplying the strains, followed by isolation of the plasmids.

Functionally complete genes, like the stilbene synthase genes according to the invention, consist of a regulatory part (in particular promotor) and the structural gene which encodes the protein stilbene synthase.

Both gene portions can be used independently of one another. For example, it is possible to arrange downstream of the regulatory portion a different DNA sequence (which deviates from the stilbene synthase gene), which is intended to be expressed after being incorporated into the plant genome. Since only a few isolated promoters are known which can become active in plants or plant cells, the promotors of the stilbene synthase genes, which are likewise parts of the present invention, represent valuable tools in the production of transformed plants or plant cells.

Likewise it is possible to arrange a "foreign" regulatory portion upstream of the stilbene synthase structural genes. This might be of advantage when, in particular plants, only certain regulatory genes (for example autologous plant genes) can become active to sufficient extent. The stilbene synthase structural genes therefore represent valuable units which can be employed on their own, and, as already explained, are likewise part of the present invention. The stilbene synthase genes according to the invention can be separated into the regulatory portions and the structural genes by the customary method. It is also possible for parts of various naturally occurring stilbene synthase genes to be combined to give novel functional "synthetic" genes (for example the above-described combination of genes 2 and 3). It is preferred to use the complete natural stilbene synthase genes (or the gene units) according to the invention.

With the aid of the customary methods, it is possible to introduce the stilbene synthase genes (or the gene units) or portions thereof, in one or more copies (for example tandem arrangement), preferably in one copy, into any procaryotic (preferably bacterial) or eucaryotic (preferably plant) DNA, as "foreign" or "additional" DNA. For example, genes 1 and 2 (or their gene units) can be incorporated together in the way in which they are arranged on plasmid pVSt12t3. The recombinant DNA which has been "modified" in this way and which can be used, for example, for transforming plants or plant cells, and which is contained in plants or plant cells after transformation, is a component of the present invention.

The stilbene synthase genes (or the gene units) and/or portions thereof, as well as the recombinant DNA, can be contained in vectors (in particular plasmids, cosmids or phages), in transformed microorganisms (preferably bacteria, in particular gram-negative bacteria such as *E. coli*) as well as in transformed plant cells and plants, or in their DNA, as "foreign" or "additional" DNA. Such vectors, transformed microorganisms (which can also contain these vectors) as well as the transformed plant cells and plants and their DNA represent components of the present invention.

As already mentioned, one or more copies of the stilbene synthase genes (or the gene units) according to the invention are incorporated into the natural plant genome (at identical or different sites of the genome), it also being possible for the different genes to be combined with each other. In the case of plants which are already capable of stilbene synthesis, the incorporation of one or more stilbene synthase genes according to the invention can lead to a considerably improved resistance behaviour. If appropriate, only the structural genes according to the invention are used, and upstream incorporation of a regulatory DNA element isolated from the respective plant may be possible.

The increased resistance to the transformed plant cells and plants according to the invention is important for agriculture and forestry, for the cultivation of ornamental plants and medicinal plants, and for plant breeding. When plant cells are cultured, for example for obtaining pharmaceutically utilizable substances, it is also advantageous to have available plant cells which have increased resistance to attack by microbial pests, in particular fungi.

The present invention therefore also relates to a process for producing transformed plant cells (including protoplasts) and plants (including parts of plants, and seeds) with increased resistance to pests, which is characterized in that (a) one or more stilbene synthase genes (or gene units) from grapevine and/or portions of the stilbene synthase genes (or the gene units) from grapevine and/or recombinant DNA according to the invention are incorporated into the genome of plant cells (including protoplasts) and, if appropriate, (b) complete transformed plants are regenerated from the transformed plant cells (including protoplasts) and, if appropriate, propagated, and, if appropriate, (c) the desired parts of the plants (including seeds) are obtained from the resulting transformed plants of the parent generation or of further generations derived therefrom.

Process steps (a), (b) and (c) can be carried out in the customary manner following known processes and methods.

Transformed plant cells (including protoplasts) and plants (including parts of plants, and seeds) which contain one or more stilbene synthase genes (or gene units) from grapevine and/or portions of the stilbene synthase genes (or of the gene units) from grapevine as "foreign" or "additional" DNA as well as those transformed plant cells and plants which can be obtained following the above process, are likewise part of the present invention.

Parts of the present invention are also the:

(a) use of the stilbene synthase genes (or of the gene units) from grapevine and/or their portions and/or the recombinant DNA according to the invention and/or the recombinant vectors according to the invention and/or the transformed microorganisms according to the invention for transforming plant cells (including protoplasts) and plants (including parts of plants, and seeds) as well as the (b) use of the plant cells (including protoplasts) and plants (including parts of plants, and seeds) transformed according to the invention for producing propagation material and for producing novel plants and propagation material thereof, and, generally, the (c) use of the stilbene synthase genes (or of the gene units) according to the invention from grapevine and/or their parts and/or the recombinant DNA according to the invention for combating pests.

A number of various methods is available for incorporating the stilbene synthase genes or the gene units or their portions into the genetic material of plants or plant cells as "foreign" or "additional" DNA. The gene transfer can be carried out following the generally customary known methods, it being possible for a person skilled in the art to determine the method which is suitable in each case without difficulty.

A particularly favourable vector which can be employed in many species which is available for transferring foreign DNA into the genomes of dicotyledonous and monocotyledonous plants is the Ti plasmid of Agrobacterium tumefaciens. The genetic material which encodes stilbene synthase is introduced into the T-DNA of suitable Ti plasmids (for example Zambryski et al. 1983) and transferred by infecting the plants, infecting parts of plants or plant tissue, such as, for example, leaf discs, stalks, hypocotyls, cotyledons, meristems and tissues derived from these such as, for example, secondary embryos and calli, or by coculturing protoplasts with Agrobacterium tumefaciens.

An alternative is the incubation of purified DNA containing the desired gene in plant protoplasts (for example Hain et al., 1985; Krens et al., 1982; Paszkowski et al., 1984) in the presence of polycations or calcium salts and polyethylene glycol.

DNA uptake can also additionally be enhanced by an electrical field (electroporation) (for example Fromm et al. 1986).

The DNA can also be incorporated in a known manner using plant pollen, by "bombarding" pollen with physically accelerated particles which carry the DNA (cf. EP-A 0,270, 356).

The plants are regenerated in a known manner with the aid of suitable media (for example Nagy and Maliga 1976).

In a preferred embodiment of the process according to the invention (in accordance with the method described in EP-A 116,718), the genes or gene units from plasmids pVSt12t3 or pVSt1 are cloned into a suitable intermediary E. coli vector for example pCV001 or pCV002, (cf. EP-A 116,718; Koncz et al. 1986) or, preferably, its derivatives, which additionally contain a reporter gene such as, for example, nptII (Herrera-Estrella et al. 1983) or hpt (Van den Elzen et al. 1986).

The plasmid of the above construction is transferred to Agrobacterium tumefaciens which contains, for example, pGV3850 or its derivatives (Zambryski et al. 1983) using customary methods (for example Van Haute et al. 1983). Genes 1 and 2 can also be transferred together in this way. As an alternative, it is possible to clone the stilbene synthase gene unit in a binary vector (for example Koncz and Schell 1986) and transfer it into a suitable Agrobacterium strain as described above (Koncz and Schell 1986). The resulting Agrobacterium strain which contains the stilbene synthase genes or gene units in a form which can be transferred to plants, is subsequently used for plant transformation.

In a further preferred embodiment, plasmid pVSt12t3 or the isolated plasmid pVSt1 or the isolated genes or gene units, if appropriate together with another plasmid containing a reporter gene for plant cells, for example for kanamycin resistance (for example Herrera-Estrella et al. 1983) or a hygromycin resistance (van den Elzen, 1986), preferably pLGVneo2103 (Hain et al. 1985), pLGV23neo (Herrera-Estrella 1983), pMON129 (Fraley R. T. et al., Proc. National Acad. Sci. U.S.A. 80, 4803 (1983), pAK1003, pAK2004 (Velten J. et al., EMBO Journ. Vol. 3, 2723 (1984) or pGSSTneo3 (pGSST3) (EP-A-189,707), is transferred to plant protoplasts in a customary manner using direct gene transfer (for example Hain et al. 1985). In this context, the plasmid(s) or the genes or gene units can be present in circular, but preferably in linear, form. When a plasmid with reporter gene is used, kanamycin-resistant protoplasts are then checked for stilbene synthase expression. In the other case (without reporter gene), the resulting calli are tested for expression of the stilbene synthase gene(s) (screening by customary methods).

Transformed (transgenic) plants or plant cells are produced by the known methods, for example by leaf-disc transformation (for example Horsch et al. 1985) by cocultivation of regenerating plant protoplasts or cell cultures with Agrobacterium tumefaciens (for example Marton et al. 1979, Hain et al. 1985) or by direct DNA-transfection. Resulting transformed plants are detected either by selection for reporter gene expression, for example by kanamycin sulphate and in vitro assay for phosphorylation of kanamycin (Reiss et al. 1984; Schreier et al. 1985) or by nopalin synthase expression (following the method of Aerts et al. 1983) or by stilbene synthase expression using Northern Blot analysis and Western Blot analysis. Stilbene synthase and the stilbenes can also be detected in transformed plants in a known manner with the aid of specific antibodies.

Stilbene synthase can also be detected by testing the enzyme activity (Rolfs et al., Plant Cell Reports 1, 83–85, 1981).

Culture of the transformed plant cells and regeneration to give complete plants are carried out by the generally customary methods with the aid of the media which are suitable in each case.

The transformed plant cells as well as the transformed plants, all of which contain the stilbene synthase genes (or the gene units) according to the invention and which are components of the present invention, show considerably increased resistance to pests, in particular phytopathogenic fungi.

The term "plants" in connection with the present invention denotes complete plants as well as parts of plants such as leaves, seeds, tubers, cuttings etc. "Plant cells" include protoplasts, cell lines, plant calli etc. "Propagation material" denotes plants and plant cells which can be used for propagating the transformed plants and plant cells, and is therefore likewise part of the present invention.

The term "DNA sequences which act in essentially the same direction" in the present connection means that the invention also comprises those modifications in which the function of the stilbene synthase genes and portions thereof are not restricted in such a way that stilbene synthase is no longer formed or that the regulatory gene portion is no longer effective. Modifications in question can be effected by the replacement, the addition and/or the removal of DNA sections, of individual codons and/or of individual nucleotides.

"Mutants" in connection with the microorganisms which can be used according to the invention denotes those modified microorganisms which still show the features which are essential for carrying out the invention, in particular the plasmids in question.

The plants to which resistance, or increased resistance, to the above pests can be imparted by incorporating the stilbene synthase genes (or the gene units) according to the invention (transformation) include virtually all plants. A particular demand for the provision of resistance is naturally in crop plants, such as forest plants, for example firs, spruces, Douglas firs, pines, larches, beeches and oaks, as well as plants which provide food and raw materials, for example cereals (in particular wheat, rye, barley, oats, millet, rice and maize), potatoes, Leguminosae such as pulses and, in particular, alfalfa, soya beans, vegetables (in particular cabbage species and tomatoes), fruit (in particular apples, pears, cherries, grapes, citrus fruits, pineapples and bananas), oil palms, tea shrubs, cocoa shrubs and coffee shrubs, tobacco, sisal and cotton, as well as in medicinal plants such as Rauwolfia and Digitalis. Crop plants which may be mentioned as particularly preferred are potatoes, tomatoes, grapevines and legumes. It is preferred to incorporate the stilbene synthase genes according to the invention into the genome of plants as "foreign" DNA (that is to say, in plants with the exception of grapevines).

Pests against which resistances, or increased resistances, can be obtained with the aid of the stilbene synthase gene according to the invention and which may be mentioned are animal pests such as insects, mites and nematodes, as well as microbial pests such as phytopathogenic fungi, bacteria and viruses. Microbial pests, in particular phytopathogenic fungi, are particularly emphasized.

The harmful insects in particular include insects from the orders of the:
Orthoptera, Dermaptera, Isoptera, Thysanoptera, Heteroptera, Homoptera, Lepidoptera, Coleoptera, Hymenoptera and Diptera.

The harmful mites include, in particular: Tarsonemus spp., Panonychus spp. and Tetranychus spp.

The harmful nematodes include, in particular: Pratylenchus spp., Heterodera spp. and Meloidogyne spp.

The microbial pests include, in particular, the phytopathogenic fungi:
Plasmodiophoromycetes, Oomycetes, Chytridiomycetes, Zygomycetes, Ascomycetes, Basidiomycetes, Deuteromycetes.

The phytopathogenic bacteria include, in particular, the Pseudomonadaceae, Rhizobiaceae, Enterobacteriaceae, Corynebacteriaceae and Streptomycetaceae.

The viral diseases include, in particular, mosaic viruses, stunting viruses and yellowing viruses.

Some causative organisms of viral, fungal and bacterial diseases which come under the generic names listed above may be mentioned as examples, but not by way of limitation:
barley yellow dwarf virus (BYDV), potato virus Y (PVY), cucumber mosaic virus (CMV), watermelon mosaic virus (WMV), tristeza virus, tobacco mosaic virus (TMV), tobacco necrosis virus (TNV), beet necrotic yellow vein virus (BNYVV) and rhizomania virus.

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides. Helminthosporium carbonum* may furthermore be mentioned.

The present invention will be illustrated in greater detail with the aid of the following exemplary embodiments:

1. Isolation of the stilbene synthase gene from grapevine

Plants and cell cultures of grapevine (*Vitis vinifera,* cv. Optima) contain the stilbene synthase genes which cause the formation of resveratrol synthase (protein size 45,000 D; reaction with specific antiserum).

For the isolation of the stilbene synthase genes, the processes and methods known in molecular biology were used as are described in detail, for example, in the following handbook: Maniatis, T., Fritsch, E. F., Sambrook, J.: Molecular Cloning: A Laboratory Manual; Cold Spring Harbor Laboratory, Second Edition 1989.

First, a "gene library" for grapevine is established: genomic DNA from enriched cell nuclei (Bedbrook, J., Plant Molecular Biology Newsletter 2, 24, 1981) is cut with the restriction enzyme NdeII in such a way that DNA fragments of an average length of about 12,000 nucleotide pairs are formed. These fragments are cloned into the BamHI site of lambda phage EMBL4 (Frischauf et al., J. Mol. Biol. 170, 827–842, 1983), and the phages are multiplied in *E. coli.* The entire phage population contains the entire genomic DNA of the grapevine cells, cloned in individual fragments, and hence also the stilbene synthases genes (multigene family).

The stilbene synthase genes, their mRNA and the cDNA of the stilbene synthases in each case contain identical nucleic acid sequences since they can be derived from each other (gene→mRNA→cDNA). This means that the stilbene synthase genes can be identified by specific hybridization with stilbene synthase cDNA (Schrbder et al. 1988; Melchior and Kindl 1990, EP-A-309 862) or with specific oligonucleotides, which can be derived from the DNA sequences indicated in EP-A-309 862. The phages with the genes are identified by hybridization and then isolated and multiplied. The genomic DNA from grapevine, which is cloned in this phage, is further mapped by analysis using various restriction enzymes, and the position of the stilbene synthase genes is determined by further hybridization experiments using cDNA sequences or synthetic oligonucleotides. Finally, gene units are cut out of the phage by digestion with EcoRI or by partial digestion with EcoRI, cloned in the appropriately cut plasmid vector pUC18 (manufacturer: Gibco-BRL GmbH, Eggenstein, Federal Republic of Germany), and multiplied as recombinant plasmids.

For isolating further stilbene synthase genes according to the invention, DNA sequences which are contained in the genes located on plasmids pVSt12t3, pVSt1 and pVSt2, can be used as probes, because of sequence homologies. For example, oligonucleotides of the following sequences can also be used, the figures indicating the position of the nucleotides relative to A of the ATG sequence, which is located at the beginning of the encoding region:

| (a) 106 | TATGC | TGATT | ACTAT | TTCAG |
| | AGTCA | CTAAG | AGCGA | GCACA T 146 |
| (b) 147 | GACTG | AGTTG | AAGAA | GAAGT |
| | TCAAT | CGCAT | ATGTA | A 183 |
| (c) 1000 | TATGG | TAACA | TGTCT | AGTGC |
| | ATGTG | TCTTG | TTTAT | TTTGG |
| | ATGAG | ATGAG | AAAGA | A 1056 |

Sequence (a) above has been designated SEQ ID NO: 1; sequence (b) above has been designated SEQ ID NO: 2; and sequence (c) above has been designated SEQ ID NO: 3. These sequences, or largely homologous sequences, are contained in the stilbene synthase genes according to the invention, so that the latter can also be characterized by a content of these sequences or by a content of sequences which are largely homologous to these sequences.

Figure 1:
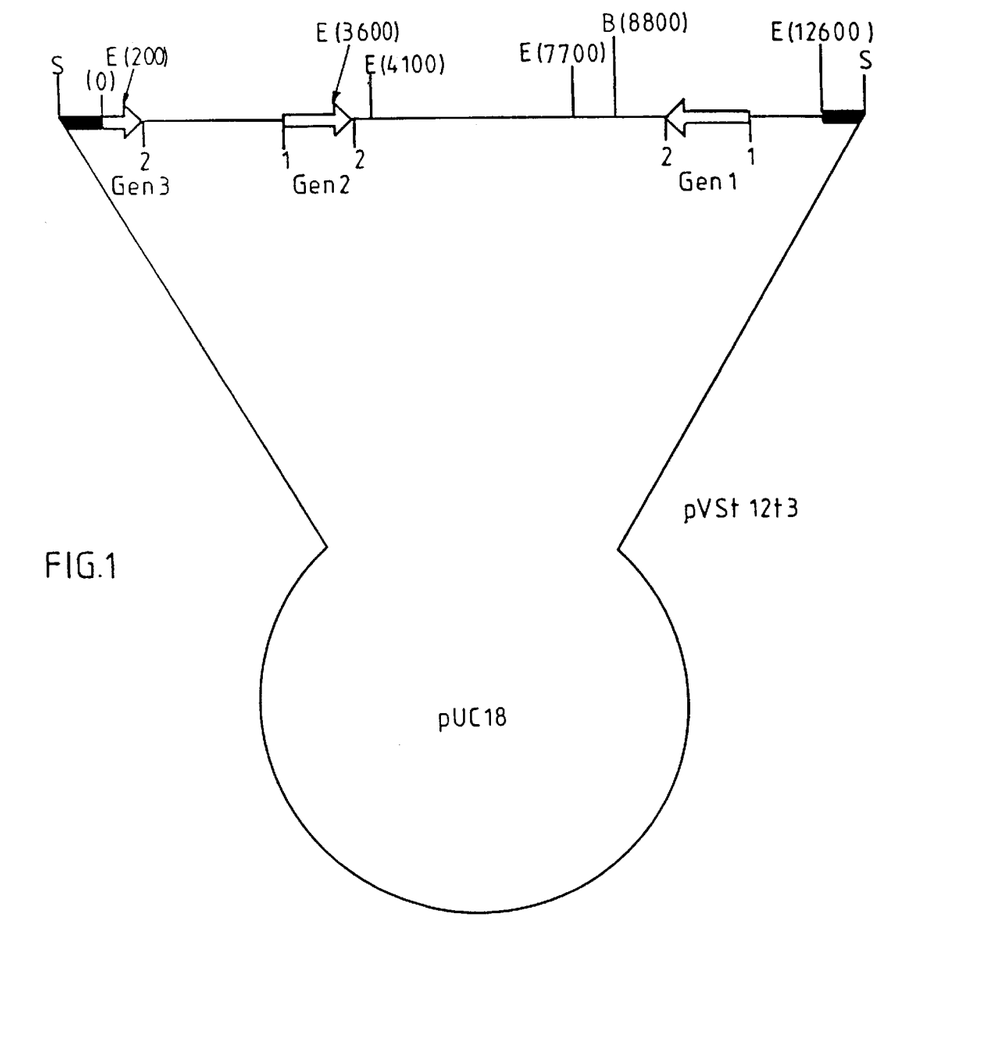
Figure 2:
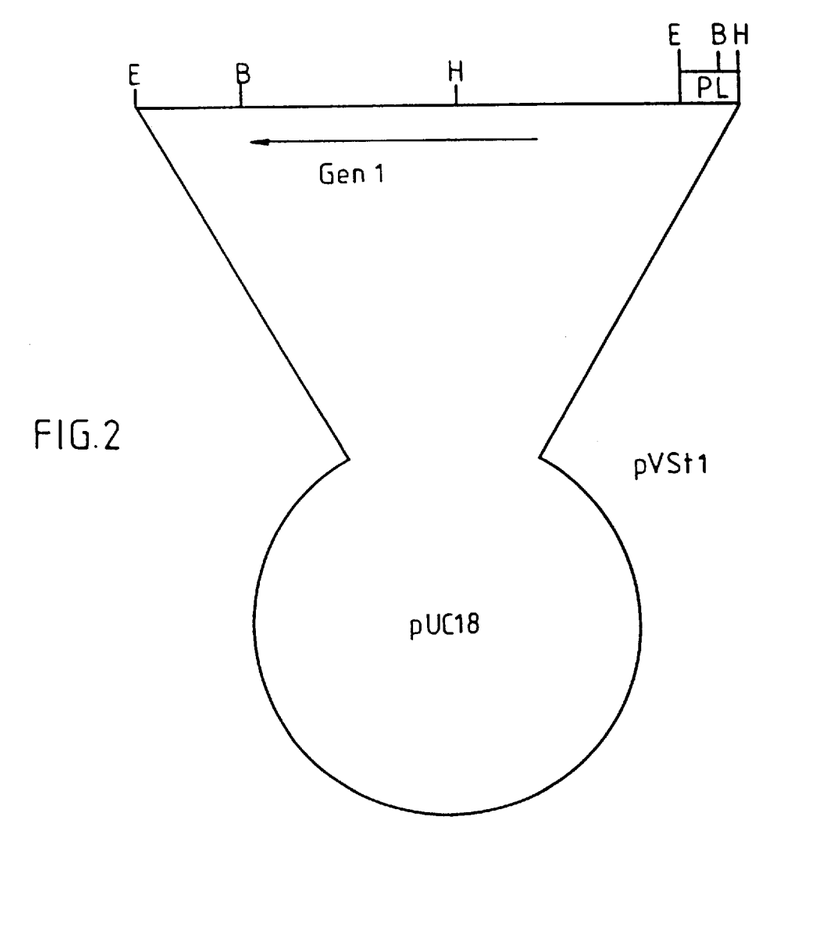
Figure 3:
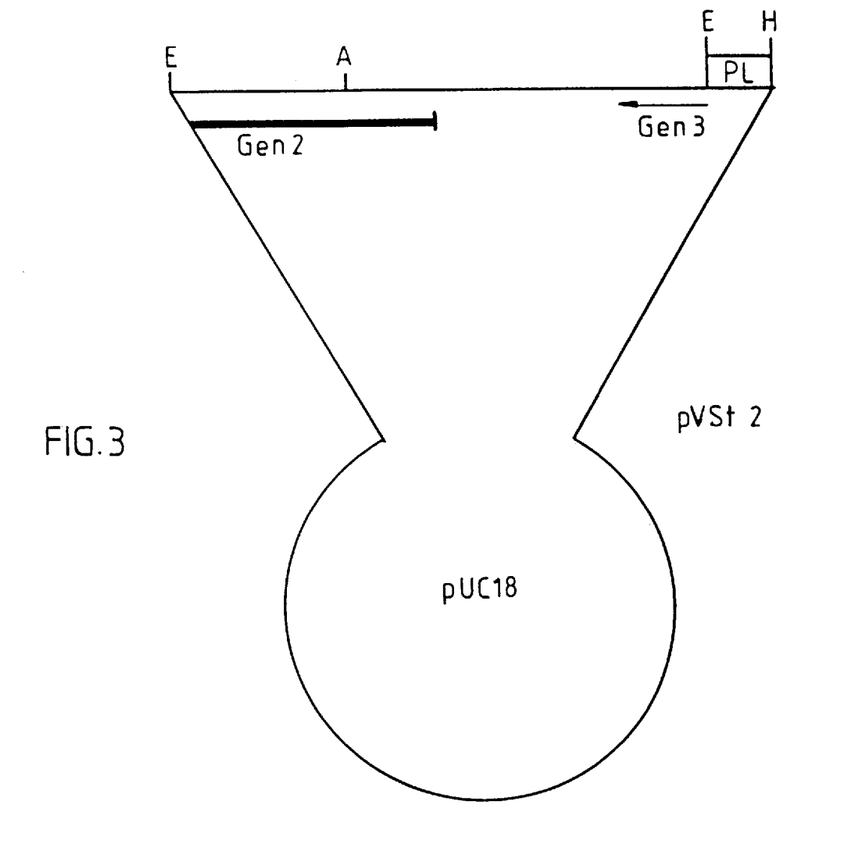
Figure 4:
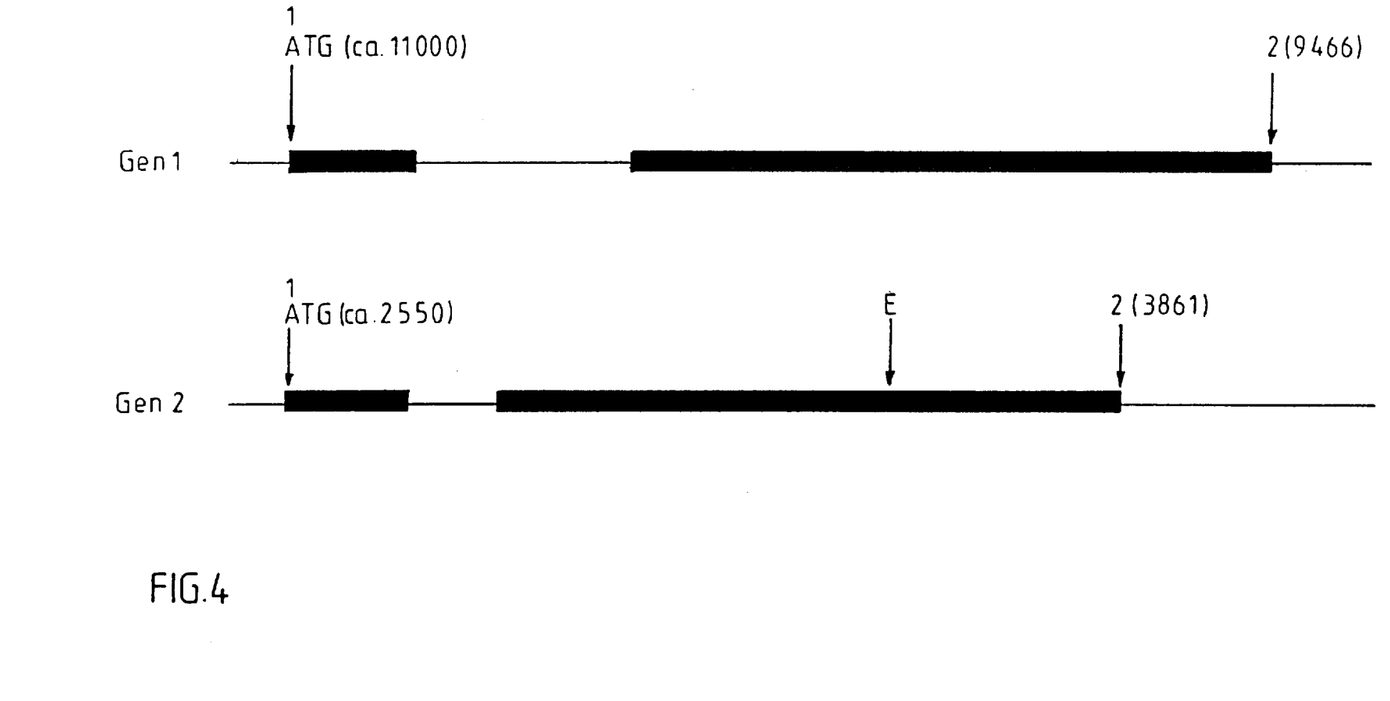
FIG. 4 represents encoding (exons/emboldened) and non-encoding areas (introns) of gene 1 and gene 2. The position of the translation initiation codon (ATG) is at approximately 11,000 (see FIG. 1) in the case of gene 1 and in position 2,550 in the case of gene 2. Gene 1 has a length of approximately 1,530 bp and ends in position 9466. Gene 2 is aprox. 1,300 bp in length and ends in position 3861. The different length of the two genes is the result of introns of different lengths.

2. Description of plasmids pVSt12t3, pVSt1 and pVSt2 (cf. FIG. 1–FIG. 3)

A.) Plasmids pVSt12t3, pVSt1 and pVSt2 consist of two components

1. Gene units or gene portions:

(a) Plasmid pVSt1:

Gene unit 1, containing the structural gene and the regulator portion of gene 1 (from grapevine, cv. Optima), is located on a nucleic acid which can be cut out from plasmid pVSt1 as a DNA fragment of (approx) 4900 bp by cleavage with the restriction enzyme EcoRI.

(b) Plasmid pVSt2:

The sequences of gene 2 and gene 3 are located on an EcoRI fragment 3.4 kb in size. Circularization of this fragment gives a functional synthetic stilbene synthase gene composed of gene portions of genes 2 and 3.

(c) Plasmid pVSt12t3:

Plasmid pVSt12t3 contains a genomic Vitis vinifera fragment of approx. 12600 bp, flanked by λ-phages DNA in vector pUC18. The complete gene units 1 and 2 are located on this fragment, which is approx. 12600 bp in size. However, not all of gene 3 is on this fragment. Gene unit 1 can be isolated by EcoRI digestion by a fragment of 4900 bp in length.

Gene unit 2 can be isolated by partial EcoRI digestion on a 3400 bp fragment.

2. Vector plasmid

The gene units or gene portions, are cloned in vector pUC18. The size of the vector is 2686 nucleotide pairs. It carries the ampicillin resistance gene, that is to say *E. coli* cells with this plasmid grow in nutrient media which contain the antibiotic ampicillin. Ori: term for sequences which are necessary for multiplying the plasmid in *E. coli.*

Plasmids pVSt1 and pVSt2 carry a gene for ampicillin resistance. They can be multiplied in a customary manner in *E. coli* cells which contain pVSt1 or pVSt2 (*E. coli* Fier 1 and Fier 2, respectively). The same applies to *E. coli* strain Fier pVstl2t3.

Preferred nutrient medium for *E. coli* cells (for example JA221, Nakamura, K., Inouye, M., EMBO J. 1, 771–775, 1982) which contain pVSt1 , pVSt2 and pVSt12t3 (*E. coli* Nurdug 2010):

| Bacto peptone* | 10 g |
| Yeast extract | 5 g |
| NaCl | 5 g |
| Agar | 20 g |
| $H_2O$ | 1 l |
| pH 7.5 | |

50 µg/ml of ampicillin are added to the nutrient medium.
Fermentation: 37° C., aerobic conditions (*Bacto is a tradename of DIFCO Lab. Detroit, USA).

3. Transformation of tobacco a) Tobacco shoot culture and isolation of tobacco protoplasts:

Nicotiana tabacum (Petit Havanna SRi) is propagated as a sterile shoot culture on hormone-free LS medium (Linsmaier and Skoog 1965). Approximately every 6–8 weeks, shoot sections are transferred to fresh LS medium. The shoot cultures are maintained in a growth cabinet at 24°–26° C. at 12 hours of light (1000–3000 Lux).

For the isolation of leaf protoplasts, about 2 g of leaves (about 3–5 cm in length) are cut into small pieces (0.5 cm×1 cm) using a new razor blade. The leaf material is incubated for 14–16 hours at room temperature in 20 ml of enzyme solution consisting of K3 medium (Nagy and Maliga 1976), 0.4 molar sucrose, pH 5.6, 2% of Zellulase R10 (Serva), 0.5% of Macerozym R10 (Serva). After this, the protoplasts are separated from cell debris by filtration over 0.30 mm and 0.1 mm steel sieves. The filtrate is centrifuged for 10 minutes at 100×g. During this centrifugation, intact protoplasts float and collect at the top edge of the enzyme solution in the form of a band. The pellet consisting of cell debris and the enzyme solution are removed by suction using a glass capillary. The precleaned protoplasts are made up to 10 ml using fresh K3 medium (0.4M of sucrose as an osmotic) and refloated. The wash medium is removed by suction, and the protoplasts are diluted to $1-2\times10^5$/ml for culturing or for subsequent infection with agrobacteria (coculture). The protoplast concentration is determined in a haemocytometer.

b) Transformation of regenerating tobacco protoplasts by coculture with Agrobacterium tumefaciens:

In what follows, the slightly modified method of Marton et al. 1979 is used. The protoplasts are isolated as described and incubated in K3 medium (0.4 molar sucrose, 0.1 mg/l NAA, 0.2 ml in K3 medium (0.4 molar sucrose, 0.1 mg/l NAA, 0.2 mg kinetin) at a density of $1-2\times10^5$/ml for 2 days in the dark and for one to two days under weak light (500 lux) at 26° C. As soon as the first protoplast divisions take place, 30 μl of an agrobacteria suspension in minimal A (Am) medium (density about $10^9$ agrobacteria/ml) are added to 3 ml of regenerating protoplasts. Coculture is effected for 3–4 days at 20° C. in the dark. The tobacco cells are then decanted into 12 ml centrifuge tubes, diluted to 10 ml with seawater (600 mOsm/kg), and pelleted for 10 minutes at 60×g. This washing process is repeated once or twice so as to remove most of the agrobacteria. The cell suspension is cultured in K3 medium (0.3 molar sucrose) with 1 mg/l NAA (naphthyl-1-acetic acid), 0.2 mg/l kinetin and 500 mg/l of the cephalosporin cefotaxim antibiotic at a density of $5\times10^4$/ml. The cell suspension is diluted every week using fresh K3 medium, and the osmotic value of the medium is gradually reduced by 0.05 molar sucrose (about 60 mOsm/kg) per week. The selection with kanamycin (100 mg/l kanamycin sulphate (Sigma), 660 mg/g active km) is initiated 2–3 weeks after coculture in agarose "bead-type culture" (Shillito et al. 1983). Kanamycin-resistant colonies can be distinguished from the background of retarded colonies 3–4 weeks after the beginning of the selection.

c) Direct transformation of tobacco protoplasts with DNA. Calcium nitrate/PEG transformation.

In a Petri dish, about $10^5$ protoplasts in 180 μl of K3 medium are carefully mixed with 20 μl aqueous DNA solution which contains 0.5 μg/μl plasmid pVSt12t3 or, for example, 0.5 μg/μl plasmid pVSt1 mixed with 0.5 μg/μl pLGV neo 2103 (Hain et al. 1985). 200 μl fusion solution (0.1 molar calcium nitrate, 0.45M of mannitol, 25% of polyethylene glycol (PEG 6000), pH 9) are subsequently added carefully. After 15 minutes, 5 ml of wash solution (0.275M of calcium nitrate, pH 6) are added and, after a further 5 minutes, the protoplasts are transferred to a centrifuge tube and pelleted at 60×g. The pellet is taken up in a small amount of K3 medium and cultured as described in the section below. Alternatively, the protoplasts can be transformed as described by Hain et al. 1985.

The transformation can also be carried out without the addition of the 0.5 μg/μl pLGVneo2103. Since no reporter gene is employed in this case, the resulting calli can be tested for the presence of the stilbene synthase gene unit with the aid of a dotblot hybridization. Hybridization probes which can be used are internal EcoRI fragments from pVSt1 or pVSt2. Other detection methods such as antibody assay or detection of an increased resistance to fungi can, of course, also be employed.

d) Culture of the protoplasts incubated together with DNA, and selection of kanamycin-resistant calli:

For the culture described below and for the selection of kanamycin-resistant colonies, a modified "bead-type culture" technique (Shillito et al. 1983) is used. One week after the protoplasts have been treated with DNA (cf. c), 3 ml of the cell suspension are mixed with 3 ml of K3 medium (0.3M of sucrose+hormones; 1.2% of (Seaplaque) LMT agarose (low-melting agarose, Marine Colloids) in 5 cm Petri dishes. For this purpose, dry agarose is autoclaved, K3 medium is added, and the mixture is briefly boiled up in a microwave oven. After the agarose has solidified, the agarose discs ("beads") together with the embedded tobacco microcalli are transferred into 10 cm Petri dishes for further culture and selection, and batches of 10 ml of K3 medium (0.3M of sucrose, 1 mg/l NAA, 0.2 mg/l kinetin) and 100 mg/l kanamycin sulphate (Sigma) are added. The liquid medium is changed every week. During this process, the osmotic value of the medium is gradually lowered.

The exchange medium (K3+km) is reduced every week by 0.05 molar sucrose (about 60 mOsm).

Selection diagram for kanamycin-resistant tobacco colonies after DNA transformation:

| 0.4M U E S | 0.3M | 0.25M | 0.20M | 0.15M K | 0.10M | Sucrose in the liquid medium |
|---|---|---|---|---|---|---|
| 1 | 2 | 3 | 4 | 5 | 6 | Weeks after DNA uptake |

(K3 medium, 1 mg of NAA, 0.2 mg of kinetin)

U=DNA uptake

E=Embedding in agarose

S=Selection with kanamycin (100 mg/l of kanamycin sulphate)

K=Kanamycin-resistant colonies can be distinguished clearly from the background e) Regeneration of kanamycin-resistant plants:

As soon as the kanamycin-resistant colonies have reached a diameter of about 0.5 cm, half of them are placed on regeneration medium (LS medium, 2% of sucrose, 0.5 mg/l benzylaminopurine BAP), and the cultures are maintained in a growth cabinet at 24° C. with 12 hours of light (3000–5000 lux). The other half is propagated as a callus culture on LS medium containing 1 mg/l NAA, 0.2 mg/l kinetin, 0.1 mg/l BAP and 100 mg/l kanamycin sulphate. When the regenerated shoots have a size of about 1 cm, they are excised and placed on ½ LS medium (1% of sucrose, 0.8% of agar) without growth regulators, for rooting. The shoots are rooted on ½ MS medium containing 100 mg/l kanamycin sulphate, and later transplanted into soil.

f.) Transformation of leaf discs by Agrobacterium tumefaciens

For the transformation of leaf discs (Horsch et al. 1985), leaves, about 2–3 cm in length, of sterile shoot cultures, are punched into discs of diameter 1 cm, and the discs are incubated for about 5 minutes with a suspension of appropriate agrobacteria (about $10^9$/ml) (cf. b) in the Am medium, see below). The infected leaf portions are maintained on MS medium (see below) without hormones for 3–4 days at about 24° C. During this time, Agrobacterium covers the leaf portions with growth. The leaf portions are subsequently washed in MS medium (0.5 mg/ml BAP, 0.1 mg/ml NAA) and placed on the same medium (0.8% of agar) containing 500 μg/ml cefotaxim and 100 μg/ml kanamycin sulphate (Sigma). The medium should be renewed after two weeks. Transformed shoots become visible after a further 2–3 weeks. The regeneration of shoots should also be carried out in parallel without selection pressure. The regenerated shoots must then be tested for transformation, using biological tests for example for nopalin synthase or stilbene synthase activity. 1–10% of transformed shoots are obtained in this manner.

Biochemical method for detecting transformation
Detection of nopalin in plant tissues Nopalin is detected as follows, as described by Otten and Schilperoort (1978) and Aerts et al. (1979). In an Eppendorf container, 50 mg of plant material (callus or leaf portions) are incubated overnight in LS medium containing 0.1M of arginine at room temperature. The plant material is then dabbed with absorbent paper, homogenized in a new Eppendorf centrifuge container using a glass rod, and the homogenate is centrifuged for 2 minutes in an Eppendorf centrifuge. 2 μl of the supernatant are applied to a sheet of paper (20×40 cm) which is suitable for electrophoresis (Whatman 3 MM paper) in the form of small spots and then dried. The sheet of paper is saturated with the mobile phase (5% of formic acid, 15% of acetic acid, 80% of $H_2O$, pH 1.8), and electrophoresis is carried out for 45 minutes at 400 V. Nopalin migrates to the cathode. The sheet of paper is then dried in a stream of hot air and pulled through phenanthrenequinone stain (equal volumes of 0.02% strength phenanthrenequinone in ethanol and 10% strength NaOH in 60% strength ethanol) in the direction of movement. The dried sheet of paper is viewed under long-wave UV light, and photographs are taken. The reagent stains arginine and arginine derivatives fluorescent yellow.

Neomycin phosphotransferase (NPT II) enzyme assay

NPT II activity in plant tissue is detected by in situ phosphorylation of kanamycin as described by Reiβet al. (1984) and modified by Schreier et al. (1985), as follows. 50 mg of plant tissue are homogenized in 50 μl of extraction buffer (10% of glycerine, 5% of 2-mercaptoethanol, 0.1% of SDS, 0.025% of bromphenol blue, 62.5 mM of tris pH 6.8) with the addition of glass powder, on ice, and the homogenate is centrifuged for 10 minutes in an Eppendorf centrifuge at 4° C. 50 μl of the supernatant are applied to a native polyacrylamide gel (145×110×1.2 mm; separating gel: 10% of acrylamide, 0.33% of bisacrylamide, 0.375M of tris pH 8.8, collecting gel: 5% of acrylamide, 0.165% of bisacrylamide, 0.125M of tris pH 6.8) and the gel is subjected to electrophoresis overnight at 4° C. and 60 V. As soon as the Bromphenol Blue marker moves out of the gel, the gel is washed twice with distilled water for 10 minutes and once with reaction buffer (67 mM tris maleate, pH 7.1, 42 mM of $MgCl_2$, 400 mM of ammonium chloride) for 30 minutes. The gel is placed on a glass plate of equal size and covered with 40 ml of 1% strength agarose in reaction buffer containing the substrates kanamycin sulphate (20 μg/ml) and 20–200 μCi $^{32}P$ ATP (Amgel is). The sandwich gel is incubated for 30 minutes at room temperature, and a sheet of phosphocellulose paper P81 (Whatman) is then placed on the agarose. Four layers of filter paper 3 MM (Whatman) and some paper towels are then placed on top of this. The transfer of in situ phosphorylated radioactive kanamycin phosphate to the P81 paper is stopped after 3–4 hours. The P81 paper is incubated for 30 minutes in a solution of Proteinase K and 1% strength sodium dodecyl sulphate (SDS) at 60° C. and then washed 3–4 times in 250 ml of 10 mM phosphate buffer pH 7.5 at 80° C., dried, and autoradiographed for 1–12 hours at −70° C. (XAR5 film, Kodak).

4. Transformation of Solanum tuberosum (potato)

The transformation was transformed precisely in the manner given in EP-A-0,242,246, pages 14 to 15, the agrobacteria containing Ti plasmids carrying the stilbene synthesis gene or the stilbene synthase genes.

All percentages in the above examples relate to per cent by weight unless indicated otherwise.

In the plant cells and plants (tobacco) obtained in accordance with the above examples, the presence of the stilbene synthase genes was confirmed by Southern Blot analysis. The expression of the stilbene synthase genes was detected by Northern Blot analysis, and stilbene synthase and stilbenes with the aid of specific antibodies. Transformed and non-transformed plants (for comparison) were sprayed with a spore suspension of Botrytis cinera, and, after 1 week, the plants were scored for fungal disease. The transformed plants showed an increased resistance to fungal disease (compared with the non-transformed comparison plants).

In what follows, some of the media employed in the transformation of plants or plant cells are described:

Am medium 3.5 g of $K_2HPO_4$
1.5 g of $KH_2PO_4$
0.5 g of $Na_3$ citrate
0.1 g of $MgSO_4 \times 7H_2O$
1 g of $(NH_4)_2SO_4$
2 g of glucose to 1 l Medium for sterile shoot culture of tobacco Macro elements ½ of the concentration of the MS salts Micro elements ½ of the concentration of the MS salts Fe EDTA Murashige and Skoog (MS)

| | |
|---|---|
| Myo-inositol | 100 mg/l |
| Sucrose | 30 g/l |
| Agar | 8 g/l |
| Vitamins | |
| Ca panthotenate | 1 mg/l |
| Biotin | 10 mg/l |
| Nicotinic acid | 1 mg/l |
| Pyridoxine | 1 mg/l |
| Thiamine | 1 mg/l |
| pH 5.7 before autoclaving | |

K3 medium

For culturing Nicotiana tabacum petit Havana SR1, Nicotiana tabacum Wisconsin 38, and *Nicotiana plumaginifolia* protoplasts (Nagy and Maliga, 1976)

| | | |
|---|---|---|
| Macro elements | $NH_4NO_3$ | 250 mg/l |
| | $KNO_3$ | 2500 mg/l |
| | $CaCl_2 \times 2H_2O$ | 900 mg/l |
| | $MgSO_4 \times 7H_2O$ | 250 mg/l |
| | $NaH_2PO_4 \times 1H_2O$ | 150 mg/l |
| | $(NH_4)_2SO_4$ | 134 mg/l |
| | $CaHPO_4 \times 1H_2O$ | 50 mg/l |
| Micro elements | $H_3BO_3$ | 3 mg/l |
| | $MnSO_4 \times 1H_2O$ | 10 mg/l |
| | $ZnSO_4 \times 4H_2O$ | 2 mg/l |
| | KI | 0.75 mg/l |
| | $Na_2MoO_4 \times 2H_2O$ | 0.25 mg/l |
| | $CuSO_4 \times 5H_2O$ | 0.025 mg/l |
| | $CoCl_2 \times 6H_2O$ | 0.025 mg/l |
| Fe-EDTA | $Na_2EDTA$ | 37.2 mg/l |
| | $FeSO_4 \times 7H_2O$ | 27.8 mg/l |
| Inositol | | 100 mg/l |

-continued

| Sucrose | | 137 g/l |
| --- | --- | --- |
| | | (= 0.4 M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l |
| pH 5.6 | | |
| Filter-sterilization | | |

Linsmaier and Skoog medium (Linsmaier and Skoog 1965)

For culturing regenerating protoplasts and for tissue culture of tobacco tumours and callus. Linsmaier and Skoog (LS) medium is Murashige and Skoog medium (Murashige and Skoog, 1962) with the following modifications:

The thiamine weighed in is more concentrated 0.4 mg/l instead of 0.1 mg/l;

No glycine, pyridoxine and nicotinic acid.

| Macro elements | $NH_4NO_3$ | 1650 mg/l |
| --- | --- | --- |
| | $KNO_3$ | 1900 mg/l |
| | $CaCl_2 \times 2H_2O$ | 440 mg/l |
| | $MgSO_4 \times 7H_2O$ | 370 mg/l |
| | $KH_2PO_4$ | 170 mg/l |
| Micro elements | $H_3BO_3$ | 6.2 mg/l |
| | $MnSO_4 \times 1H_2O$ | 22.3 mg/l |
| | $ZnSO_4 \times 4H_2O$ | 8.6 mg/l |
| | KI | 0.83 mg/l |
| | $Na_2MoO_4 \times 2H_2O$ | 0.25 mg/l |
| | $CuSO_4 \times 5H_2O$ | 0.025 mg/l |
| | $CoCl_2 \times 6H_2O$ | 0.025 mg/l |
| Fe-EDTA | $Na_2EDTA$ | 37.2 mg/l |
| | $FeSO_4 \times 7H_2O$ | 27.8 mg/l |
| Inositol | | 100 mg/l |
| Sucrose | | 30 g/l |
| Agar | | 8 g/l |
| Vitamins | Thiamine | 0.4 mg/l |
| Hormones: | NAA | 1 mg/l |
| | Kinetin | 0.2 mg/l |
| pH 5.7 before autoclaving | | |

The following literature on the transformation of plants or plant cells may be cited:

Aerts M, Jacobs M, Hernalsteens J. P., Van Montagu M, Schell J (1983) Induction and in vitro culture of *Arabidopsis thaliana* crown gall tumours. Plant Sci Lett. 17: 43–50

Fraley R. T., Rogers S. G., Horsch R. B., Sanders P. R., Flick J. S., Adams S. P., Bittner M. L., Brand L. A., Fink C. L., Fry J. S., Fallupi G. R., Goldberg S. B., Hoffmann N. L., Woo S. C. (1983). Expression of bacterial genes in plant cells. Proc. Natl. Acad. Sci. USA 80:4803–4807.

Fromm M. E., Taylor L. P., Walbot V. (1986) Stable transformation of maize after gene transfer by electroporation. Nature 319: 791–793

Hain, R., Stabel, P., Czernilofsky, A. P., Steinbiβ, H. H., Herrera-Estrella, L., Schell, J. (1985) Uptake, integration, expression and genetic transmission of a selectable chimeric gene by plant protoplasts. Molec Gen Genet. 199: 161–168

Hain R., Bieseler B., Kindl H., Schröder G., Stöcker R. (1990) Expression of a stilbene synthase gene in *Nicotiana tabacum* results in synthesis of the phytoalexin resveratrol. Plant Mol, Biol. 15:325–336.

Hernalsteens J. P., Thia-Tong L., Schell J., Van Montagu M. (1984) An Agrobacterium-transformed Cell culture from the monocot *Asparagus officinalis*. EMBO J. 3:3039–3041

Herrera-Estrella L., De Block M., Messens E., Hernalsteens J. P., van Montagu M., Schell J. (1983) EMBO J. 2: 987–995.

Horsch R. B., Fry J. E., Hoffmann N. L., Eichholtz D., Rogers S. G., Fraley R. T. (1985) A simple and general method for transferring genes into plants. Science 277: 1229–1231

Krens F. H., Molendijk L, Wullems G. J., Schilperoort R. A. (1982) in vitro transformation of plant protoplasts with Ti plasmid DNA. Nature 296: 72–74

Koncz C., Schell J. (1986) The promoter of $T_L$-DNA gene 5 controls the tissue-specific expression of chimaeric genes carried by a noval type of *Agrobacterium linary* vector. Mol. Gen. Genet. (1986) 204: 338–396

Linsmaier D. M., Skoog F. (1965) Organic growth factor requirements of tobacco tissue cultures. Physiol Plant 18: 100–127

Marton L., Wullems G. J., Molendijk L., Schilperoort P. R. (1979) In vitro transformation of cultured cells from *Nicotiana tabacum* by *Agrobacterium tumefaciens*. Nature 277: 1229–131

Melchior F., Kindl H. (1990) Grapevine stilbene synthase cDNA only slightly differing from chalcone synthase cDNA is expressed in *Escherichia coli* into a catalytically active enzyme FEBS 268:17–20

Nagy J. I., Maliga P. (1976) Callus induction and plant regeneration from mesophyll protoplasts of *Nicotiana sylvestris*. Z Pflanzenphysiol 78: 453–455

Otten LABM, Schilperoort R. A. (1978) A rapid microscale method for the detection of Lysopin and Nopalin dehydrogenase activities. Biochim biophys acta 527: 497–500

Paszkowski J., Shillito R. D., Saul M., Mandak V., Hohn T., Hohn B., Potrykus I. (1984) Direct gene transfer to plants. EMBO J 3: 2717–2722

Rolf, C. H., Fritzemeier K. H. and Kindl H. (1981) Cultured cells of Arachis hypogaea susceptible to induction of stilbene synthase (resveratrol forming) Plant Cell. Rep. 1:83–85

Schröder, G., Brown J. W. S. and Schröder, J. (1988) Molecular analysis of resveratrol synthase: cDNA, genomic clones and relationship with chalconsynthase. Eur. J. Biochem. 172, 161–169

Shillito R. D., Paszkowski J. Potrykus I. (1983) Agarose plating and Bead type culture technique enable and stimulate development of protoplast-derived colonies in an number of plant species. Pl Cell Rep 2: 244–247

Van den Elzen P. J. M., Townsend J., Lee K. Y., Bedbrook J. R. (1985) A chimaeric resistance gen as a selectable marker in plant cells. Plant Mol. Biol. 5, 299–302.

Velten J., Velten L., Hain R., Schell J. (1984) Isolation of a dual plant promotor fragment from the Ti Plasmid of *Agrobacterium tumefaciens*. EMBO J 12: 2723–2730

Van Haute E., Joos H., Maes M., Warren G., Van Montagu M., Schell J. (1983) Intergenic transfer and excharge recombination of restriction fragments clones in pBR 322: a novel strategy for the reversed genetics of Ti plasmids of /Agrobacterium tumefacines. EMBO J 2: 411–418.

Zambryski P., Joos H., Genetello C., van Montagu M., Schell J. (1983) Ti-plasmid vector for the introduction of DNA into plant cells without altering their normal regeneration capacity, EMBO J 12: 2143–2150.

Reiss, B., Sprengel, Will H., and Schaller H. (1984) A new sensitive method for qualitative and quantitative assay of neomycin phosphotransferase in crude cell tracts, GENE 1081: 211–217

Schreier P. H., Seftor E. A., Schell J. and Bohnert H. J. (1985) The use of nuclear-encoded sequences to direct the light-regulated synthesis and transport of a foreign protein into plant chloroplasts, EMBO J Vol. 4, No. 1: 25–32

The following published patent applications can furthermore be listed:

| | |
|---|---|
| EP-A-116,718 | EP-A-126,546 |
| EP-A-159,418 | EP-A-164,597 |
| EP-A-120,515 | EP-A-175,966 |
| EP-A-120,516 | WO 84/02913 |
| EP-A-172,112 | WO 84/02919 |
| EP-A-140,556 | WO 84/02920 |
| EP-A-174,166 | WO 83/01176 |
| EP-A-122,791 | |

BRIEF DESCRIPTION OF DRAWINGS

FIG. 1 represents plasmid pVSt12t3. The stilbene synthase gene units 1 and 2 are located on a Vitis DNA fragment, approx. 12,600 bp in length, which, flanked in pVSt12t3 by λ-phage DNA, had been cloned into the SmaI site of pUC18. Only terminal sequences of gene 3 are located on pVSt12t3. 1 in each case denotes the beginning of the encoding region, and 2 the end of the encoding region, of gene 1, gene 2 and gene 3. In addition, the arrows indicate how the genes are orientated on the fragment. The emboldened areas represent flanking phage DNA.

FIG. 2 represents plasmid pVSt1. Gene 1 is located on the EcoRI fragment, approx. 4.9 kb in size. It can also be isolated by double digestion with BamHI and EcoRI. HindIII cuts within the gene. The arrow indicates how the gene is orientated on the plasmid.

FIG. 3 represents plasmid pVSt2. This plasmid contains an EcoRI fragment of pVSt12t3, 3.4 kb in size, which contains the terminal areas of gene 3 and the proximal areas of gene 2. Circularization of this fragment results in a functional stilbene synthase gene. This gene is a synthetic gene of gene 2 and gene 3.

In FIGS. 1–4, the symbols denote:
E : EcoRI
B : BamHI
H : HindIII
PL : Polylinker from plasmid pUC18
A : Asp718
ATG : Translation initiation codon
S : SmaI The increased resistance of plants which have been transformed according to the invention will be illustrated with the aid of the following example:

Example A

To test for an increased resistance to plant diseases, the plants were inoculated with a pathogen, and the degree of infection was used as the parameter. The test pathogen used was *Botrytis cinerea* Pers.

The tobacco plants were precultured by tissue culture and subsequently potted in the greenhouse in standard soil (manufactured by Balster) in pots (d=11 cm), and raised in the greenhouse at 23° C. and 70–80% relative atmospheric humidity until the tests were started. They were supplied with water and fertilizer as required. For inoculation, the leaves of the plants (3–4 weeks after transferral to the greenhouse) were sprayed to runoff point with a spore suspension of the pathogen. The plants were then incubated at 100% relative atmospheric humidity and 10°–20° C. After 4–8 days, the health of the plants was determined as a percentage, based on the infected leaf area.

As can be seen from the tables, transformed tobacco plants, in which a stilbene synthase gene according to the invention was introduced, were infected with *B. cinerea* to a lesser degree than those of the non-transformed wild type SR1, and therefore showed an increased resistance to fungi in comparison with the non-transformed control plants.

Table

Effect of the resveratrol gene on infection of the tobacco plants with *Botrytis cinerea*.

| | % infected leaf area on leaf No. | | | | | | | |
|---|---|---|---|---|---|---|---|---|
| | 1 | 2 | 3 | 4 | 5 | 6 | x̄ | Reduction* |
| Wild type (control) | 15.0 | 16.0 | 16.5 | 11.5 | 8.6 | 2.8 | 11.7 | |
| Transformed tobacco 1 | 6.4 | 8.6 | 8.8 | 2.9 | 1.7 | 0.9 | 4.9 | 58% |
| Transformed tobacco 2 | 10.8 | 8.1 | 3.7 | 3.6 | 3.0 | 0.8 | 5.0 | 57% |

* Reduction calculated using Abbott's formula
x̄ = Average

We claim:

1. A method of isolating a stilbene synthase gene from grapevine (Vitis) comprising the steps of:
   (a) extracting plasmid pVSt1 from *E. coli* strain Fier pVSt1 (DSM6002);
   (b) treating said plasmid with a restriction enzyme to release the grapevine DNA insert contained on said plasmid;
   (c) subjecting grapevine genomic DNA, cDNA or RNA, to said grapevine DNA insert under hybridization conditions; and
   (d) screening for stable hybrids resulting from (c).

2. A method of isolating a stilbene synthase gene from grapevine (Vitis) comprising the steps of:
   (a) extracting plasmid pVSt2 from *E. coli* strain Fier pVSt2 (DSM6003);
   (b) treating said plasmid with a restriction enzyme to release the grapevine DNA insert contained on said plasmid;
   (c) subjecting grapevine genomic DNA, cDNA or RNA, to said grapevine DNA insert under hybridization conditions; and
   (d) screening for stable hybrids resulting from (c).

3. A method of isolating a stilbene synthase gene from grapevine (Vitis) comprising the steps of:
   (a) extracting plasmid pVSt12t3 from *E. coli* strain Fier pVSt12t3 (DSM6346);
   (b) treating said plasmid with a restriction enzyme to release the grapevine DNA insert contained on said plasmid;
   (c) subjecting grapevine genomic DNA, cDNA or RNA, to said grapevine DNA insert under hybridization conditions; and
   (d) screening for stable hybrids resulting from (c).

4. A method of isolating a stilbene synthase gene from grapevine (Vitis) comprising the steps of:
   (a) subjecting grapevine genomic DNA, cDNA or RNA under hybridization conditions to a hybridization probe comprising a nucleotide sequence selected from the group consisting of:
   TATGCTGATTACTATTTCAGAGTCAC-TAAGAGCGAGCACAT (Seq. ID No. 1);
   GACTGAGTTGAAGAAGAAGTTCAATCG-CATATGTAA (Seq. ID No. 2); and
   TATGGTAAKTGTCTAGTGKTGTGTCT-TGTTTATTTTGGATGAGATGAGAAAGAA (Seq. ID No. 3);
   (b) screening for stable hybrids resulting from (a).

* * * * *

UNITED STATES PATENT AND TRADEMARK OFFICE
CERTIFICATE OF CORRECTION

PATENT NO. : 5,834,268
DATED : November 10, 1998
INVENTOR(S) : Rudiger Hain et al It is certified that error appears in the above-identified patent and that said Letters Patent is hereby corrected as shown below:

Column 20, Claim 4, Line 11    After "TATGGTAA" delete "K" and substitute --CA--, after "TGTCTAGTG" delete "K" and substitute --CA--

Signed and Sealed this

Twenty-second Day of June, 1999

Attest:

Q. TODD DICKINSON

*Attesting Officer*    *Acting Commissioner of Patents and Trademarks*